(12) United States Patent
Ehlert

(10) Patent No.: US 8,827,972 B2
(45) Date of Patent: Sep. 9, 2014

(54) SUCTION PUMP SYSTEM

(75) Inventor: Hilmar Ehlert, Hergiswil (CH)

(73) Assignee: Medela Holding AG, Baar (CH)

( * ) Notice: Subject to any disclaimer, the term of this patent is extended or adjusted under 35 U.S.C. 154(b) by 162 days.

(21) Appl. No.: 13/186,642

(22) Filed: Jul. 20, 2011

(65) Prior Publication Data

US 2012/0029448 A1 Feb. 2, 2012

(30) Foreign Application Priority Data

Jul. 30, 2010 (CH) ...................................... 1255/10

(51) Int. Cl.
*A61M 1/00* (2006.01)

(52) U.S. Cl.
CPC ......... *A61M 1/0001* (2013.01); *A61M 2205/84* (2013.01); *A61M 1/0066* (2013.01)
USPC ............................ 604/319; 604/313; 604/317

(58) Field of Classification Search
USPC ........... 604/317–326, 35, 313, 315, 540–543; 417/2, 3–8, 62
See application file for complete search history.

(56) References Cited

U.S. PATENT DOCUMENTS

| | | | |
|---|---|---|---|
| H1324 H * | 6/1994 | Dalke et al. ...................... 604/65 |
| 5,971,711 A * | 10/1999 | Noji et al. ........................... 417/2 |
| 6,764,462 B2 * | 7/2004 | Risk et al. ......................... 604/67 |
| 2009/0005747 A1 | 1/2009 | Michaels et al. |

FOREIGN PATENT DOCUMENTS

| | | |
|---|---|---|
| EP | 1166805 | 1/2002 |
| WO | 2007/070570 | 6/2007 |
| WO | 2007/128156 | 11/2007 |

OTHER PUBLICATIONS

International Search Report for International Patent App. No. PCT/CH2011/000159, dated Oct. 31, 2011.
Swiss Search Report for CH App. No. 1255/2010 dated Nov. 19, 2010.

* cited by examiner

*Primary Examiner* — Loan H Thanh
*Assistant Examiner* — Jennifer M Deichl
(74) *Attorney, Agent, or Firm* — McDonnell Boehnen Hulbert & Berghoff LLP

(57) ABSTRACT

A suction pump system for aspirating body fluids from a patient is disclosed. The suction pump system includes a housing, at least one pump unit, and a one fluid collection container, which is connected to the pump unit via a vacuum line. The at least one pump unit is arranged in the housing, and the housing has more than one fixture for releasably and simultaneously holding the fluid collection container. The suction pump system allows a patient's body fluids to be aspirated from different sites simultaneously. The suction pump system is easy to operate, affords the user great flexibility in terms of the choice of drainage, and permits a good overview of the chosen applications.

14 Claims, 4 Drawing Sheets

SUCTION PUMP SYSTEM

CROSS REFERENCE TO RELATED APPLICATIONS

The present application claims priority to Swiss Patent Application No. 01255/10 filed Jul. 30, 2010, the entire contents of which are incorporated herein by reference.

TECHNICAL FIELD

The present invention relates to a suction pump system.

BACKGROUND

Stationary suction systems are normally used in the medical field to aspirate body fluids from body cavities or wounds. These suction systems basically comprise a suction source, in particular a vacuum pump, a fluid or secretion collection container, a surge tank arranged therebetween, and connection lines, in particular a drainage or secretion line leading from the patient to the fluid collection container, a connection line leading from the collection container to the surge tank, and a vacuum line connecting the surge tank to the suction source.

For the purposes of the healing process, it has now been found to be important for the patient to be able to move about unaided and leave bed as soon as possible. For this reason, portable suction systems have become known, which are used for the most part in wound drainage. WO 2007/128156 discloses a portable suction pump unit of this kind. It has a housing, with a pump unit arranged therein, and a fluid collection container. This container is connected releasably to the housing by being swiveled into and held in corresponding guides of two protruding side walls of the housing. A drainage hose, with its patient-side end designed as an adapter, can be plugged into the housing and thus connected to the fluid collection container.

Appliances of this type have proven useful in practice. Specialists in this field have been working specifically on creating a pump which is as small as possible, compact and quiet and can be used for a large number of applications, and which should also be easy to operate.

However, no practical solution is available to patients from whom body fluids are to be aspirated from different sites. If a single pump is used with a branched hose, there is an increased risk of the hose becoming blocked in the area of the Y-shaped connector piece. If several appliances are used, this increases the costs of treatment, and the nursing personnel have to operate and monitor a large number of appliances.

SUMMARY

It is therefore an object of the invention to make available a suction pump system which is suitable for aspirating a patient's body fluids from different sites simultaneously.

The suction pump system according to the invention for aspirating body fluids from a patient has a housing, at least one pump unit, and at least one fluid collection container, which is connected to the pump unit via a vacuum line. The at least one pump unit is arranged in the housing, and the housing has more than one fixture for releasably and simultaneously holding the fluid collection container.

Since more than one fluid collection container can be connected to the housing, more than one hose can be used. These hoses can therefore be routed to different sites on the patient and can aspirate fluids from different body cavities or from different locations in the same body cavity.

The fluid collection containers can be secured in or on the housing in a manner known per se. In particular, they can be swiveled in or pushed in or can be positioned and secured on the housing by way of indirect connecting elements.

Fluids are understood here as, among other things, all types of body fluids, including secretions and fat, such as those that can arise, for example, during surgery, in wound drainage, in thoracic drainage, and in liposuction.

The suction pump system according to the invention can be used in particular for cardio drainage and for pleura drainage. Both types of drainage can be carried out simultaneously using the same system according to the invention.

The system is preferably portable.

It is advantageous that, by increasing the number of the fluid collection containers, the capacity for the amount of body fluid to be collected is increased. Since each site or each body cavity to be aspirated can be assigned its own fluid collection container, it is also possible to better monitor the nature and quantity of the aspirated fluid. The latter is not mixed with fluids from other aspiration sites. However, it is still possible to combine several aspiration sites in groups and route their aspirated fluids into the same fluid collection container.

It is preferable, however, for each fluid collection container to be connected to the patient via its own drainage hose. Each drainage hose is preferably connected to its own fluid collection container such that, in the mathematical sense, there is a one-to-one connection between fluid collection container and body cavity. This makes analysis and monitoring easier for the medical personnel, since it is possible to determine for each fluid collection site, on the basis of the associated fluid collection container, which type of fluid is being collected and in what quantities.

By virtue of the suction pump system according to the invention, there is therefore no longer any need for branching of the hoses and, consequently, for Y-shaped connector pieces for hoses. This therefore minimizes the risk of the hoses becoming blocked, as often occurs at the Y-shaped connector pieces in particular.

In a preferred embodiment, the fixtures arranged on the appliance and receiving the fluid collection containers are designed identically. The system can use fluid collection containers that are designed identically and of the same size. However, it can also receive different fluid collection containers. The differences can lie, for example, in the shape, in the size, in the nature of the filters, in the nature of the fluid clotting means, or in the nature of the sensors arranged in or on the container.

However, the system can also be provided with differently designed fixtures in each of which only suitably shaped fluid collection containers can be received.

The fixtures are preferably arranged next to one another.

In a simple embodiment, only a single pump unit with a single vacuum pump is arranged in the housing. This pump is connected to the fluid collection containers via internal vacuum lines running inside the housing or via external vacuum lines running outside the housing. This simple embodiment has the advantage of being inexpensive, relatively light in weight and relatively small.

In other embodiments, at least two pump units or vacuum pumps are arranged in the housing. Each of these vacuum pumps is connected to at least one fluid collection container via internal or external vacuum lines. Here too, a one-to-one connection is preferred, such that each fluid collection container is assigned its own pump. This system has the advantage that, if one pump fails, it is possible to change to another pump in the same housing.

It is also possible for one pump to apply a vacuum to several fluid collection containers.

At least one control electronics unit, also called a PCB (printed circuit board), is arranged in the housing. The control electronics unit serves to operate the pump unit by processing and using signals obtained from possible sensors. In a simple embodiment, one control electronics unit is assigned to several or all of the pump units and therefore operates several or all of the vacuum pumps. This reduces the costs. In other embodiments, each pump unit, i.e. each vacuum pump, is assigned to its own control electronics unit. There is therefore once again a one-to-one correspondence. It is also possible for several groups of pump units to be formed, which are assigned to their own control electronics unit. The different controls can be mounted on the same circuit board. However, each control preferably has its own circuit board. If several controls are used, these can be optimized for the corresponding application, for example cardio drainage or pleura drainage. Moreover, if a pump or control electronics unit fails, the other pump is still able to function.

The system has at least one input and display unit. If several units are present, they are preferably each assigned to a single fluid collection container and/or to a single pump unit. However, they can also be assigned to groups thereof.

At least one battery for powering the electronics and the pump motor is preferably present in the housing. A single battery can be provided for all the pumps, or each pump can be assigned its own battery. Moreover, one group of pumps can also be connected to one battery, and another group to another battery. Connection to the public power supply is also possible.

Modules of the above-mentioned individual elements are preferably present, which are combined to form a common system in a common housing. These modules each comprise, for example, one pump unit, one fluid collection container, one control electronics unit, one input and display unit and, optionally, one battery. At least the input and display unit and the associated fluid collection container are preferably arranged such that a user can form a clear relationship of the input and display units to the corresponding fluid collection container.

All the modules preferably have the same width, such that there is a uniform division of the housing. In this way, the individual modules can be easily exchanged. It is possible, for example, using the same structural parts, to assemble a system that has two cardio applications and one pleura application, and another system that has one cardio application and two pleura applications.

An advantage of the system according to the invention is that a single appliance affords the user many possibilities and is easy to operate. The physician or the nursing personnel can decide which and how many of the available drainage containers to use. He can also choose the size of the drainage containers. The physician or the nursing staff can decide how many pumps should be used and what kind of pumps and what kind of control. Using the same appliance, he can carry out pleura drainage and cardio drainage and other types of drainage simultaneously.

BRIEF DESCRIPTION OF THE FIGURES

Preferred embodiments of the invention are described below with reference to the drawings, which serve only for explanatory purposes and are not to be interpreted as limiting the invention. In the drawings.

DETAILED DESCRIPTION

Figure 1:
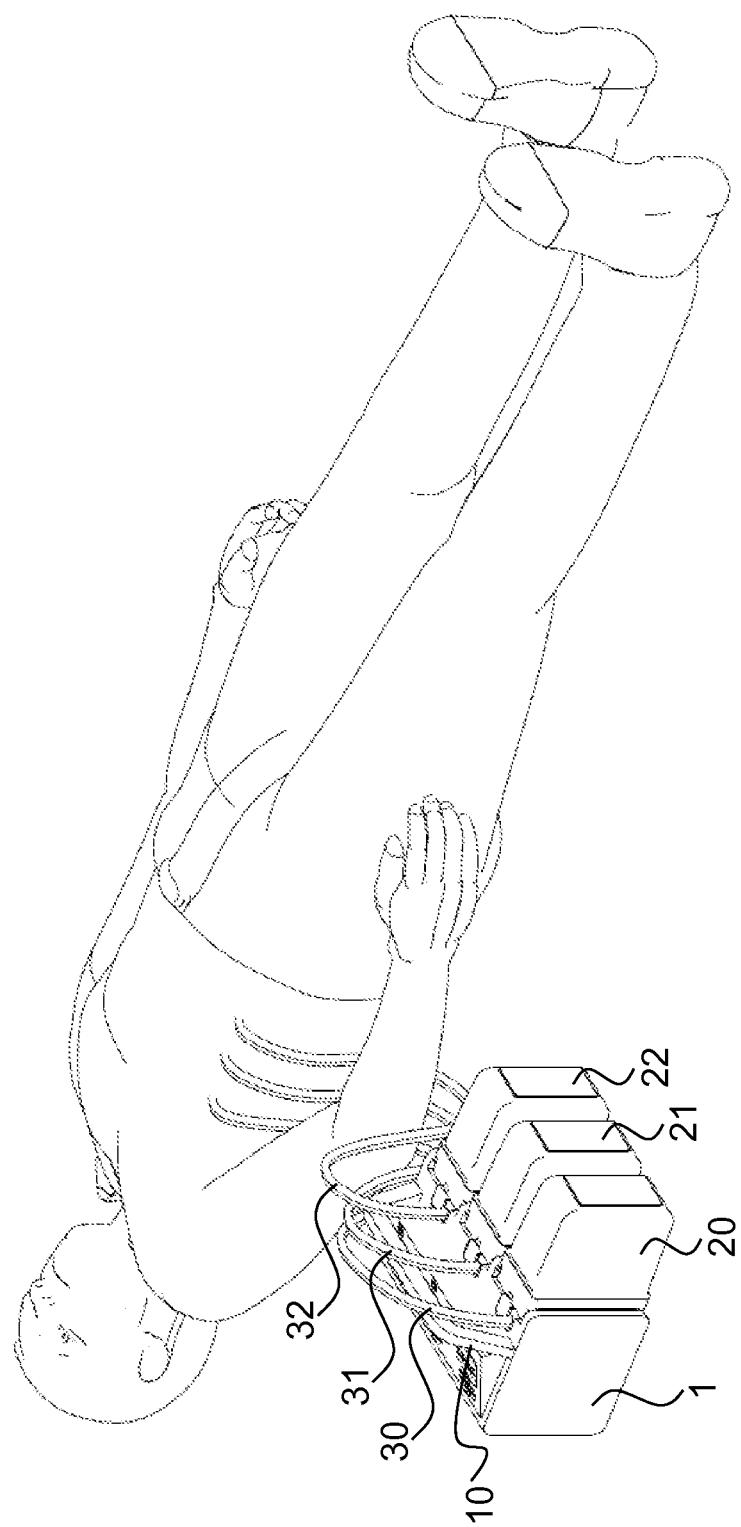
FIG. 1 shows a schematic view of a suction pump system according to the invention in a first embodiment, during use on a patient.

A first example of a suction pump system according to the invention is shown in FIG. 1. The suction pump system is designed as a portable appliance. The suction pump system has a housing 1 with a carrying handle 10 by which the appliance is designed to be carried. At least one pump unit, i.e. a vacuum pump, is arranged in the housing 1. Fluid collection containers 20, 21, 22 can be secured on the housing 1. Here, they are held in their position by means of catches 120, 121, 122, which can be seen in FIG. 3. The housing 1 preferably has a fixture into which the collection containers 20, 21, 22 can be pushed or pivoted to their intended position of use. The fluid collection containers 20, 21, 22 are preferably arranged next to one another, with all the fixtures being of the same design.

Secretion hoses, here called drainage hoses 30, 31, 32, are also present. The drainage hoses 30, 31, 32 lead to a patient and can be single-lumen or multi-lumen hoses. Each hose has a drainage line. A service line with a smaller diameter is preferably also present and is used, for example, to flush the line.

Figure 3:
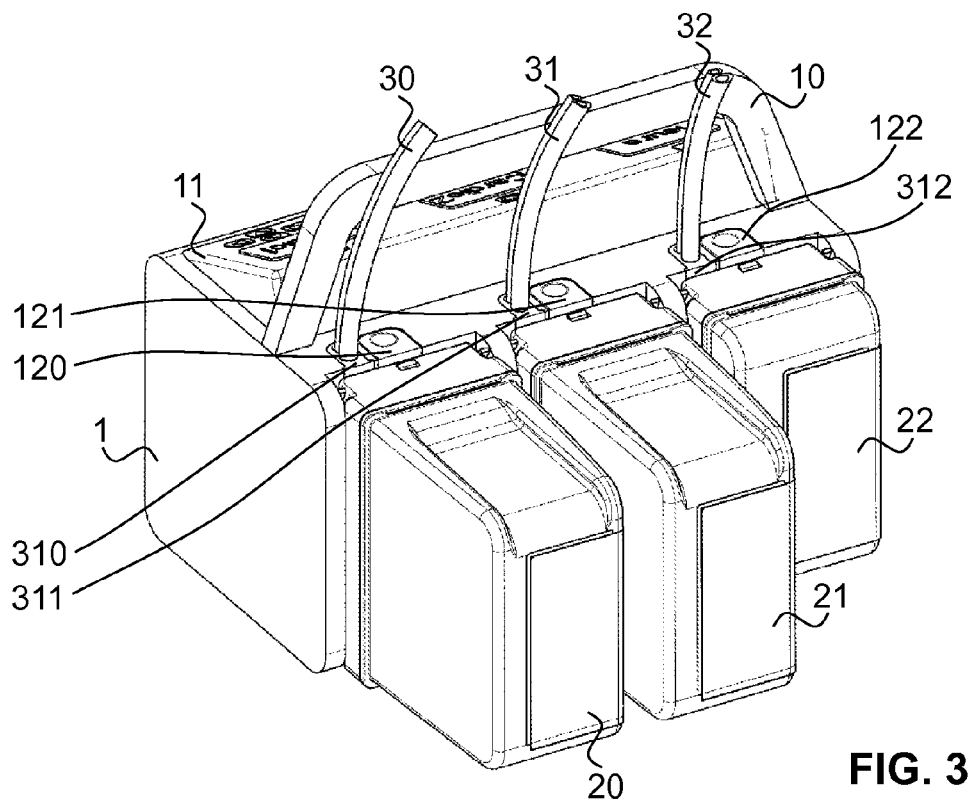
FIG. 3 shows the suction pump system according to FIG. 2 from a second side.

As can be seen from FIG. 3, the pump-side ends of the drainage hoses 30, 31, 32 are connected to coupling parts 310, 311, 312, which can be plugged into the housing 1 and each establish a drainage connection to a respectively adjacent fluid collection container 20, 21, 22.

During use, a vacuum or underpressure is generated in the respective fluid collection container 20, 21, 22 by means of the vacuum pump and of a vacuum line extending through the housing 1. By means of the fluid collection container 20, 21, 22 being connected to the respective drainage hose 30, 31, 32, an underpressure is created in the body cavity of the patient. Body fluid is aspirated through the drainage hose 30, 31, 32 into the fluid collection container 20, 21, 22 and collected there.

It is also possible to plug the drainage hoses 30, 31, 32 directly into the fluid collection containers 20, 21, 22 instead of into the housing 1. Moreover, it is possible for drainage hoses 30, 31, 32 to be connected to the respective fluid collection container 20, 21, 22 in such a way that the connection cannot be undone without being destroyed. This is advantageous, since the fluid collection containers 20, 21, 22 and also the drainage hoses 30, 31, 32 are disposable products, which have to be discarded in the correct way after use. By contrast, the housing 1 with the at least one vacuum pump can be used more than once.

The drainage hoses 30, 31, 32, in particular the drainage lines, are preferably unbranched, such that a 1:1 connection between fluid collection container 20, 21, 22 and the patient can be established. The hoses can be routed to different sites on the patient's body.

In the example according to FIG. 1, all the fluid collection containers 20, 21, 22 are of the same design and, in particular, are of the same size and the same capacity. In the example according to FIGS. 2 and 3, one of the fluid collection containers 22 is smaller and has a smaller capacity than the two other fluid collection containers 20, 21. Other size ratios can also be chosen and/or each fluid collection container can be designed with another capacity or shape. The fixtures in the housing 1 are preferably designed such that the same fixture can receive fluid collection containers of different sizes.

Figure 2:
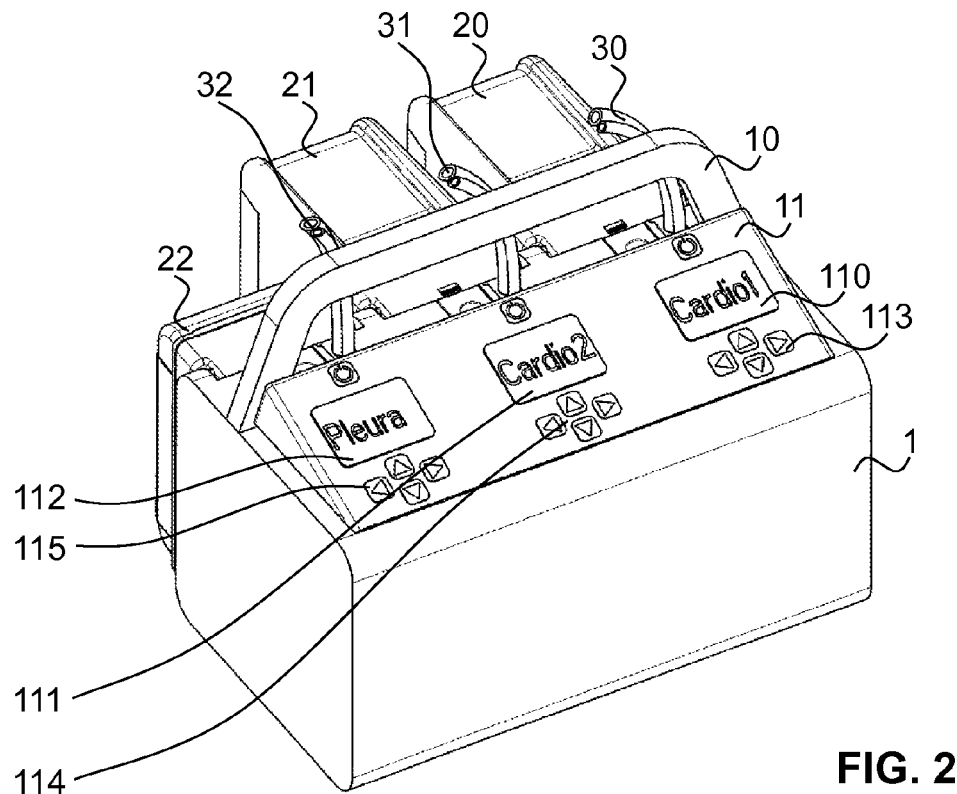
FIG. 2 shows a schematic and perspective view of a suction pump system according to the invention in a second embodiment, seen from a first side.

In FIGS. 2 and 3, a console 11 can be seen on the housing 1, the console 11 having at least one input and display unit. In this example, the console 11 has a sloping design. The display preferably has a display surface 110, 111, 112. The input fields 113, 114, 115 can be input keys, as shown here, rotary knobs or other suitable means.

The illustrative embodiments shown in FIGS. 1 to 3 are designed as modules. The display surface 112, the input field 115 and the fluid collection container 22 can be unambiguously assigned to one another. This also applies to the other display surfaces, input fields and fluid collection containers. At least the individual outer elements of the modules, i.e. the abovementioned elements including the associated fixtures of the housing 1, are preferably arranged next to one another. This gives a better overview and makes it easier to assign the elements.

Thus, as can be seen from FIGS. 2 and 3, different drainage applications can be carried out simultaneously using the same appliance. The display 112 shows pleura drainage, and the displays 110, 111 show two different cardio drainages.

Figure 4:
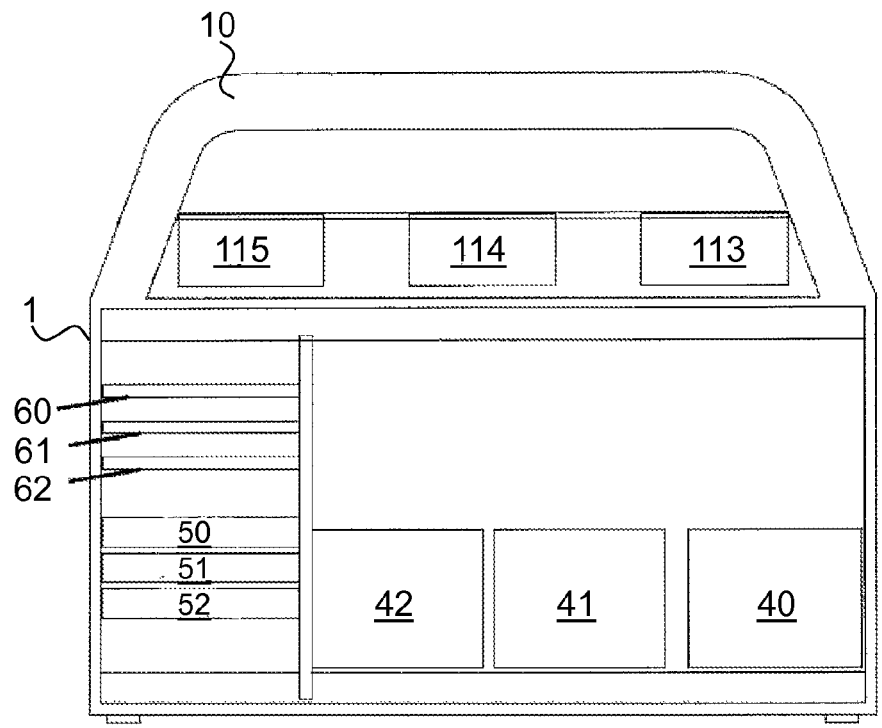
FIG. 4 shows a schematic view of the suction pump system according to FIG. 2.

The inside of the housing 1 is shown schematically in FIG. 4. In this illustrative embodiment, three pump units or vacuum pumps 40, 41, 42 are present, which are each operated by a control electronics unit 60, 61, 62 assigned only to this pump. There is also a one-to-one relationship of the input and display units 113, 114, 115 and of the fluid collection containers 20, 21, 22 (not shown here).

Batteries 50, 51, 52 and/or a power supply for connection to an external mains supply are also present which, in this example, are likewise in a one-to-one relationship to a respective module.

Figure 5:
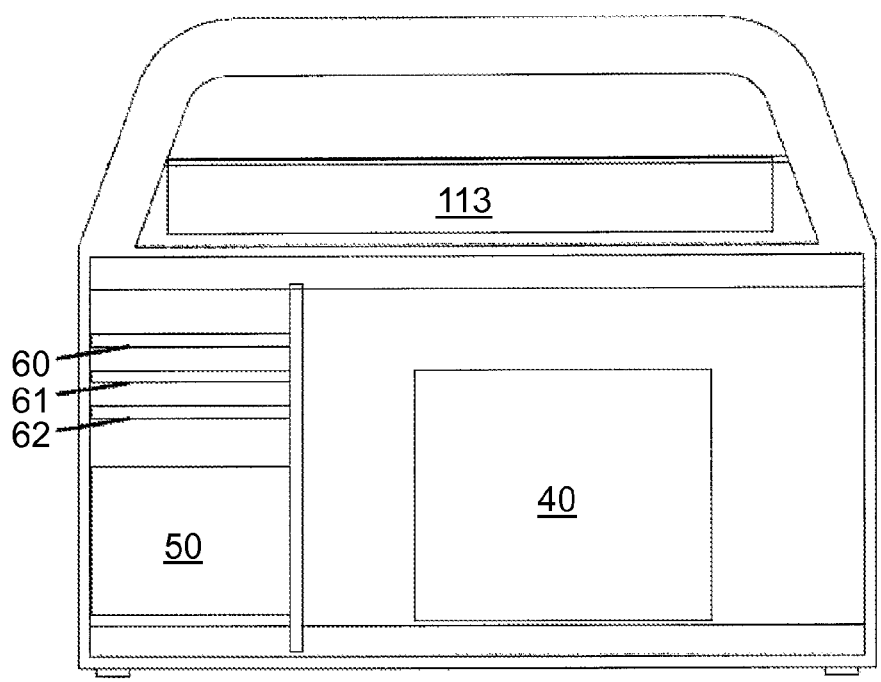
FIG. 5 shows a schematic view of the suction pump system according to the invention in a third embodiment.

In FIG. 5, there is only one vacuum pump 40, only one battery 50 or only one power pack, and only one display and input unit 113 for all the fluid collection containers. However, as before, there are three control electronics units 60, 61, 62. In this way, it is still possible, as shown in FIGS. 2 and 3, to carry out different drainage applications simultaneously, these drainage applications being shown on the same display and being generated by the same vacuum pump.

Figure 6:
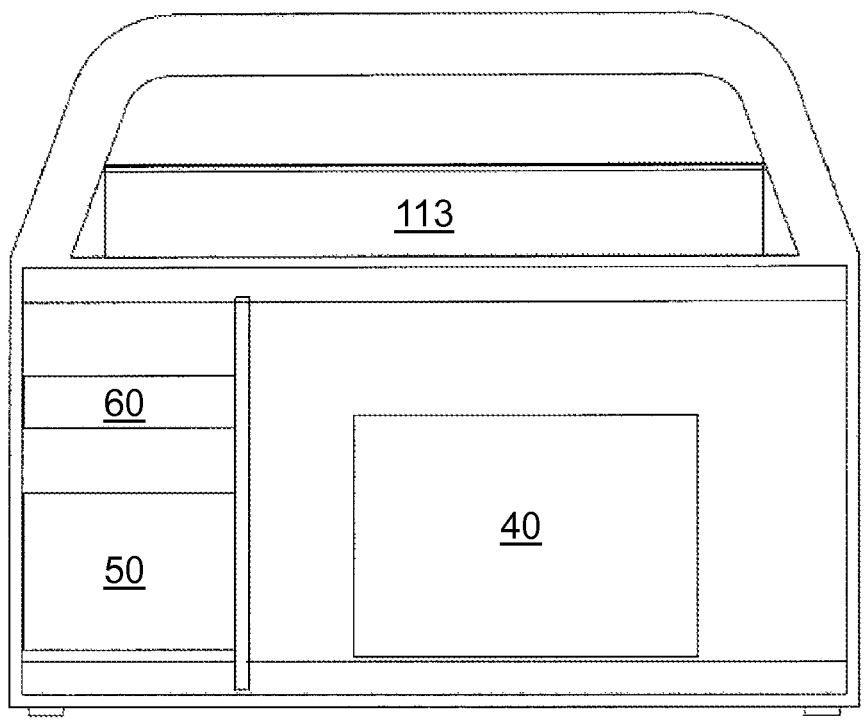
FIG. 6 shows a schematic view of the suction pump system according to the invention in a fourth embodiment.

In the illustrative embodiment according to FIG. 6, there is also just a single control electronics unit, preferably just a single PCB.

Further combinations of the individual elements of the system are possible. In the embodiments described, three fluid collection containers were held in the same housing. Other numbers are possible, in particular two, four or more containers. Any desired number of individual elements can be chosen, and the number does not have to correspond to the number of elements of another type. For example, two pumps can be used in combination with three containers.

The suction pump system according to the invention allows a patient's body fluids to be aspirated from different sites simultaneously. It is easy to operate, affords the user great flexibility in terms of the choice of drainage, and permits a good overview of the chosen applications.

The invention claimed is:

1. A suction pump system for aspirating body fluids from a patient, the suction pump system having:
    a housing with an upper side and a side wall,
    at least one pump unit,
    a first and at least one second input and display unit being arranged on the upper side of the housing, and
    at least a first fluid collection container,
    the at least one pump unit being arranged in the housing, and the housing having a first and
    at least one second fixture, the first fluid collection container being releasably held in the first fixture and each of the at least one second fixture being capable of simultaneously holding a further fluid collection container,
    wherein said first fixture and said at least one second fixture are arranged next to one another in the side wall of the housing,
    wherein the first fluid collection container and the at least one further fluid collection container are arranged next to each other protruding the side wall of the housing in the same direction, each of the first fluid collection container and the at least one second fluid collection container being at least partially visible when arranged in the fixtures,
    wherein the first input and display unit and the at least one second input and display unit are arranged next to each other in a line, thereby forming a parallel line to the arrangement of the first and the at least one second fluid collection containers,
    wherein the first input and display unit is assigned to the first fluid collection container and is arranged opposite to the first fluid collection container, and
    wherein each of the at least one second input and display unit is assigned to one of the at least one second fluid collection container and is arranged opposite to the one of the at least one second fluid collection container.

2. The suction pump system as claimed in claim 1, further comprising drainage lines for connecting the fluid collection containers to the patient, wherein each drainage line is connected to a separate one of said fluid collection containers.

3. The suction pump system as claimed in claim 1, wherein said first fixture and said at least one second fixture are identical.

4. The suction pump system as claimed in claim 1, wherein at least two pump units are arranged in the housing.

5. The suction pump system as claimed in claim 4, wherein each of said fluid collection containers is assigned to a separate one of said pump units.

6. The suction pump system as claimed in claim 1, wherein more than one of said fluid collection containers is assigned to one single of said at least one pump unit.

7. The suction pump system as claimed in claim 6, wherein all of said fluid collection containers are assigned to the same of said at least one pump unit.

8. The suction pump system as claimed in claim 1, wherein at least one control electronics unit is arranged in the housing.

9. The suction pump system as claimed in claim 8, further comprising a group of said pump units, wherein all pump units of said group are assigned to a single one of said at least one control electronics unit.

10. The suction pump system as claimed in claim 9, wherein all of said pump units of the suction pump system are assigned to a single one of said control electronics unit.

11. The suction pump system as claimed in claim 8, wherein each pump unit is assigned to a separate one of said control electronics unit.

12. The suction pump system as claimed in claim 1, wherein one of said at least one pump unit, one of said fluid collection containers, a control electronics unit and a input and display unit form a module, and at least two such modules are present.

13. The suction pump system as claimed in claim 1, wherein the system is portable.

14. The suction pump system as claimed in claim 1, wherein the fixtures hold simultaneously the fluid collection containers.

\* \* \* \* \*